United States Patent
Schubart

(10) Patent No.: US 6,316,622 B1
(45) Date of Patent: Nov. 13, 2001

(54) PROCESS FOR PREPARING CIS-2,6-DIMETHYLPIPERAZINE

(75) Inventor: Rüdiger Schubart, Bergisch Glasdbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/504,141

(22) Filed: Feb. 15, 2000

(30) Foreign Application Priority Data

Feb. 24, 1999 (DE) .............................. 199 07 829

(51) Int. Cl.$^7$ .................................. C07D 241/04
(52) U.S. Cl. ............................................ 544/358
(58) Field of Search .............................. 544/358

(56) References Cited

U.S. PATENT DOCUMENTS

| | | | |
|---|---|---|---|
| 2,525,223 | 10/1950 | Howard | 260/268 |
| 2,911,407 | 11/1959 | Langdon et al. | 260/268 |
| 3,112,318 | 11/1963 | Lemon et al. | 260/268 |
| 3,692,789 | 9/1972 | Lichtenwalter et al. | 260/268 SY |
| 4,224,248 | 9/1980 | Birkenstock et al. | 260/580 |
| 4,287,365 | 9/1981 | Becker et al. | 564/422 |
| 4,792,626 | 12/1988 | Becher et al. | 564/422 |
| 5,253,993 | 10/1993 | Birkenstock et al. | 425/78 |

FOREIGN PATENT DOCUMENTS

| | | |
|---|---|---|
| 902570 | 8/1962 | (GB) . |
| 1295784 | 11/1972 | (GB) . |
| 8-34773 | 2/1996 | (JP) . |

OTHER PUBLICATIONS

Arzneim–Forsch/Drug Res. 41 (11), Nr. 7, (month unavailable) 1991, pp. 744–746, A. Kagemoto et al, Synthesis of [Carbonyl–$^{14}$C]Sparfloxacin.

Primary Examiner—Emily Bernhardt
(74) Attorney, Agent, or Firm—Joseph C. Gil; Richard E. L. Henderson

(57) ABSTRACT

This invention relates to a process for the selective preparation of cis-2,6-dimethylpiperazine by reacting (i) a diisopropanolamine mixture comprising compounds having the formulas $HN(CH_2CH(OH)CH_3)_2$, $HN(CH(CH_3)CH_2OH)_2$, and $HN(CH(CH_3)CH_2OH)(CH_2CH(OH)CH_3)$ or (ii) 1,2-diaminopropane with ammonia and hydrogen in the presence of a hydrogenation catalyst.

12 Claims, No Drawings

PROCESS FOR PREPARING CIS-2,6-DIMETHYLPIPERAZINE

BACKGROUND OF THE INVENTION

The present invention relates to a process for preparing cis-2,6-dimethylpiperazine by reacting diisopropanolamine or 1,2-diaminopropane with ammonia and hydrogen in the presence of a catalyst.

Substituted piperazines are useful intermediates for the synthesis of rubber processing aids, in particular of vulcanization accelerators, and for the synthesis of crop protection agents and pharmacologically active compounds. Cis-2,6-dimethylpiperazine, for example, is an important starting material for the synthesis of certain antibacterial quinolonecarboxylic acid derivatives such as sparfloxacin (Arzneim.-Forsch., 41, 744–746 (1991)). Accordingly, the preparation of substituted piperazines, particularly cis-2,6-dimethylpiperazine, is of increasing importance.

British Patent 1,295,784 describes a process for preparing N-(2-aminoethyl)piperazine by cyclization of aminoethanol in aqueous medium in the presence of ammonia, hydrogen, and a catalyst. When carrying out this process, it is essential that a fraction of the reaction mixture is, after distillative removal of as much of the desired N-(2-aminoethyl) piperazine as is possible, recycled into the reaction. This measure allows the N-(2-aminoethyl)piperazine yield to be increased considerably.

U.S. Pat. No. 3,692,789 likewise discloses a process for preparing N-(2-aminoethyl)piperazine. In the presence of ammonia, hydrogen, and a hydrogenation catalyst, N-(hydroxyethyl)diethylenetriamine is cyclized to give N-(2-aminoethyl)piperazine.

According to U.S. Pat. No. 3,112,318, the synthesis of piperazine from aminoethanol is carried out in the presence of ammonia, hydrogen, and a hydrogenation catalyst. In this process, it is important to operate in the absence of water. By-products formed in the reaction are ethylenediamine and N-(2-aminoethyl)piperazine.

In contrast to the piperazine mentioned above, as well as to nitrogen-substituted piperazines, 2,6-dimethylpiperazine has two asymmetric carbon atoms in positions 2 and 6. Accordingly, two stereo-isomers, trans- and cis-2,6-dimethylpiperazine, exist, both of which can in principle be formed in synthesis reactions.

U.S. Pat. No. 2,525,223 discloses a process for preparing mono-N-alkylpiperazines by reacting dialkanolamines in the form of diethanolamine or its alkyl derivatives with a primary alkylamine in the presence of a catalyst, such as, for example, Raney nickel. The experiments described in the patent are exclusively reactions of diethanolamine with methyl-, ethyl-, or isopropylamine to give mono-N-(methyl-, ethyl-, or isopropyl)-piperazine. The conversions obtained in these reactions are very low, being at most 34%. With respect to di(2-hydroxypropyl)amine, which is mentioned in principle as a starting material, no further statements, particularly about which products and stereoisomers are formed during the reaction, are made.

Japanese Laid-Open Publication Hei 8-34773 discloses a process for preparing cis-2,6-dimethylpiperazine starting from diisopropanolamine. This diisopropanolamine is pure diisopropanolamine of the structure $HN(CH_2CH(OH)CH_3)_2$ (i.e., di(2-hydroxypropyl)amine) since, in the course of the reaction, only the formation of cis- and trans-2,6-dimethylpiperazine is reported. If, in addition to the $HN—(CH_2—CH(OH)CH_3)_2$, $HN(CH(CH_3)—CH_2OH)(CH_2CH(OH)CH_3)$ were also present, cis- and trans-2,5-dimethylpiperazine would also have to have been formed as products of the cyclization reaction. The pure uniform diisopropanolamine is initially reacted in an organic solvent in the presence of a catalyst with ammonia and hydrogen. Preferred organic solvents are aromatic hydrocarbons, such as benzene, toluene, or xylene. The mixture of cis-2,6- and trans-2,6-dimethylpiperazine formed during the cyclization in the organic solvent is initially separated from the catalyst by filtration, then freed from water by azeotropic distillation and, after further addition of organic solvent, subjected to crystallization. The crystallized cis-2,6-dimethylpiperazine is separated. Some of the trans-2,6-dimethylpiperazine that remains in the reaction mixture can subsequently be isomerized in the presence of a catalyst at a temperature of at least 180° C. to give cis-2,6-dimethyl-piperazine, with the overall yield of cis-2,6-dimethylpiperazine thereby being increased. The presence of the organic solvent is emphasized as being decisive for the selectivity of the primary cyclization for the cis-2,6-dimethylpiperazine. Thus, in the cyclization of diisopropanolamine of the formula $HN(CH_2CH(OH)CH_3)_2$ with Raney nickel in the presence of toluene, a selectivity of 81 to 82% is achieved. In contrast, in the presence of water instead of toluene, a selectivity of only 72% for the cis-2,6-di-methylpiperazine is achieved.

U.S. Pat. No. 2,911,407 describes another process for preparing 2,6-dimethylpiperazine with conversions of an order of magnitude of 70%. To this end, di(2-hydroxypropyl)amine is reacted under pressure with ammonia in the presence of a nickel- or cobalt-containing hydrogenation/dehydrogenation catalyst, using at least 1 mol of ammonia per mole of di(2-hydroxypropyl)amine. Preferred catalysts are Raney nickel and Raney cobalt. U.S. Pat. No. 2,911,407 does not indicate whether and in what proportions the isolated 2,6-dimethylpiperazine contains the two cis- and trans-stereoisomers. Moreover, the 2,6-dimethylpiperazine is not separated into the two stereoisomers.

British Patent 902,570 discloses a process for preparing C-alkylsubstituted piperazines from di(2-hydroxyalkyl) amines having at least one secondary hydroxyl group. According to the description and the Examples of GB 902,570, these di(2-hydroxyalkyl)amines, such as diisopropanolamine in the form of di(2-hydroxypropyl)amine, 1-(2-hydroxyethylamino)-2-propanol, or 3,3-imino-di-2-butanol, are always employed in pure form and not as mixtures of different isomers. The catalyst used in the reaction must comprise at least one metal or metal oxide from the group consisting of nickel, copper, and cobalt. Additionally, it may comprise small amounts of chromium oxide, molybdenum oxide, manganese oxide, thorium oxide, or mixtures thereof as promoters. Reaction of di(2-hydroxypropyl)amine with ammonia and hydrogen in the presence of a hydrogenation catalyst made of nickel, copper, and chromium oxides gives 2,6-dimethylpiperazine, the conversion obtained in Example II being above 90% and the yield of 2,6-dimethylpiperazine being 74.3%. However, like the above-mentioned U.S. Pat. No. 2,911,407, GB 902,570 contains no statements about whether and in what proportions the isolated 2,6-dimethylpiperazine is composed of the two cis- and trans-stereoisomers, and the 2,6-dimethylpiperazine is not separated into the two stereoisomers.

In the synthesis of 2,6-dimethylpiperazine, each of the above-mentioned processes employs pure substances such as di-(2-hydroxypropyl)amine, for which isolation is always complicated, as starting materials. Moreover, little is known about the targeted and selective preparation of cis-2,6-dimethylpiperazine and only a few options are available.

Accordingly, it was an object of the present invention to provide a process that, using more easily obtainable starting materials, makes it possible to obtain the pure cis-2,6-dimethylpiperazine stereoisomer in a selective preparation.

SUMMARY OF THE INVENTION

The present invention relates to a process for preparing cis-2,6-dimethylpiperazine comprising reacting (i) a diisopropanolamine mixture comprising compounds having the formulas $HN(CH_2CH(OH)CH_3)_2$, $HN(CH(CH_3)CH_2OH)_2$, and $HN(CH(CH_3)CH_2OH)(CH_2CH(OH)CH_3)$ or (ii) 1,2-diaminopropane with ammonia and hydrogen in the presence of a hydrogenation catalyst.

DETAILED DESCRIPTION OF THE INVENTION

The diisopropanolamine mixture used in the process according to the invention, which comprises compounds having the formulas $HN(CH_2CH(OH)CH_3)_2$, $HN(CH(CH_3)CH_2OH)_2$, and $HN(CH(CH_3)CH_2OH)$— $(CH_2CH(OH)CH_3)$, is obtained, for example, in the reaction of propylene oxide with ammonia to give propanolamine. The triisopropanolamine and the monoisopropanolamine which may, depending on how the reaction is carried out, also be formed in this reaction are separated off, so that the resulting diisopropanol mixture to be used in the process according to the invention no longer contains monoisopropanolamine and triisopropanolamine. The compounds represented by the formulas $HN(CH_2CH(OH)CH_3)_2$, $HN(CH(CH_3)CH_2OH)_2$, and $HN(CH(CH_3)CH_2OH)(CH_2CH(OH)CH_3)$ are three isomers. Of these, the compounds represented by the formulas $HN(CH_2CH(OH)CH_3)_2$ and $HN(CH(CH_3)CH_2OH)_2$ each comprise two optical antipodes and the compound represented by $HN(CH(CH_3)CH_2OH)(CH_2CH(OH)CH_3)$ comprises four optical antipodes. Preferably, the diisopropanolamine mixture used comprises at least 85% by weight of $HN\text{—}(CH_2\text{—}CH(OH)(CH_3)_2$ 5–10% by weight of $HN(CH(CH_3)\text{—}CH_2OH)(CH_2\text{—}CH(OH)(CH_3)$ and 0.1–2% by weight of $HN\text{—}(CH(CH_3)\text{—}CH_2OH)_2$.

Particularly preferably, the diisopropanolamine mixture used comprises

86–94% by weight of $HN\text{—}(CH_2\text{—}CH(OH)CH_3)_2$

8–10% by weight of $HN(CH(CH_3)\text{—}CH_2OH)(CH_2\text{—}CH(OH)CH_3)$ and 0.1–1% by weight of $HN\text{—}(CH(CH_3)\text{—}CH_2OH)_2$.

Very particularly preferably, the diisopropanolamine mixture used comprises

87–89% by weight of $HN\text{—}(CH_2\text{—}CH(OH)CH_3)_2$

8–10% by weight of $HN(CH(CH_3)\text{—}CH_2OH)(CH_2\text{—}CH(OH)CH_3)$ and 0.1–1% by weight of $HN\text{—}(CH(CH_3)\text{—}CH_2\text{—}OH)_2$.

The sum of the % by weight mentioned above for the diisopropanolamine mixtures in question is in particular 97, preferably 98, particularly preferably 99 and in particular 100% by weight. 1,2-Diaminopropane is commercially available.

It is surprising that the process according to the invention succeeds in forming cis-2,6-dimethylpiperazine with excellent selectivity and at the same time a very good yield when this mixture of a large number of in total 8 diisopropanolamine isomers is used.

Suitable hydrogenation catalysts are hydrogenation catalysts known from the prior art. Preference is given to using commercial Raney catalysts, with particular preference being given to Raney nickel and Raney cobalt. Catalysts that comprise at least one metal or metal oxide from the group consisting of nickel, copper, cobalt, and iron have also found to be useful. Particular preference is given to nickel- and iron-containing catalysts, particularly those having a nickel content of at least 60% by weight and an iron content of at most 40% by weight, such as, for example, Ni/Fe 85/15, Ni/Fe 70/30, Ni/Fe 66/6, or Ni/Fe 68/6. The hydrogenation catalysts can be used in unsupported form or else applied to customary supports such as silica gel, $Al_2O_3$, or $SiO_2$. Furthermore, the hydrogenation catalysts may also comprise small amounts of chromium oxide, molybdenum oxide, manganese oxide, thorium oxide, or mixtures thereof as promoters. Such catalysts are described, for example, in German Offenlegungsschriften 4,026,351, 2,713,374, 2,713,373, and 3,537,247.

About 5 to 150 g (preferably 20 to 100 g and particularly preferably 30 to 50 g) of catalyst are employed per mole of diisopropanolamine mixture or 1,2-diaminopropane.

Ammonia is usually added under pressure in pure liquid form in an amount of 100 to 200 ml (4 to 8 mol), preferably 110 to 160 ml (4.4 to 6.4 mol), per mole of diisopropanolamine mixture or 1,2-diaminopropane. However, it is also possible to use aqueous ammonia solutions.

Hydrogen is added at a pressure of 1 to 12 MPa (preferably of 2.5 to 10 MPa). The reaction is carried out at a temperature of 100 to 250° C. (preferably 150 to 220° C. and particularly 190 to 210° C.) over a period of 2 to 10 hours (preferably 2.5 to 5 hours).

The presence of other organic solvents in the process according to the invention is not imperative but is possible. It is possible to use aromatic hydrocarbons, such as benzene, toluene, or xylene, aliphatic hydrocarbons, such as n-hexane or cyclohexane, aliphatic alcohols, such as methanol, ethanol, or isopropanol, or ethers, such as dioxane, dibutyl ether, or morpholine. The reaction can also be carried out in the presence of water if aqueous ammonia solution is used.

With reductive amination/dehydrogenating cyclization of the diisopropanolamine mixture defined above or of 1,2-diaminopropane, the reaction according to the invention gives a reaction mixture of the different isomers of cis/trans-2,6-dimethylpiperazine and cis/trans-2,5-dimethylpiperazine, said mixture comprising at least 85% by weight of cis-2,6-dimethylpiperazine and at most 15% by weight of the other isomers (trans-2,6-, cis-2,5-, and trans-2,5-dimethylpiperazine). This selectivity for cis-2,6-dimethylpiperazine, which is already high, can be improved even further by distilling the mixture of the trans-2,6-, cis-2,5-, and trans-2,5-isomers and then recrystallizing at least once as described below. After distillation and two-fold recrystallization, it is possible to obtain essentially 100% pure cis-2,6-dimethylpiperazine. The overall yield of the process is at least 60% (preferably at least 65%) of cis-2,6-dimethylpiperazine, based on the diisopropanolamine mixture employed.

The distilled reaction mixture is recrystallized using a mixture of one or more aliphatic alcohols and one or more hydrocarbons as solvent. Suitable aliphatic alcohols are, for example, isopropanol, isobutanol, or isoamyl alcohol, preference being given to isopropanol. Suitable hydrocarbons were found to be, for example, light benzine or petroleum ether, preference being given to using light benzine. Alcohols and hydrocarbons are employed in a ratio by volume of (0.5–9.5):10 (preferably (0.5–6):10, particularly preferably (0.5–2):10). Particular preference is given to carrying out a twofold recrystallization from an isopropanol/light benzine mixture in a ratio by volume of 1:10.

If the starting material used is 1,2-diaminopropane, a dimethyl-piperazine isomer mixture comprising 18.3% cis-2,5-dimethylpiperazine, 13.7% trans-2,5-dimethylpiperazine, 43.7% cis-2,6-dimethylpiperazine, and 5.7% trans-2,6-dimethylpiperazine is obtained, for example, under the stated process conditions in the presence of Raney nickel at 200° C.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

In the Examples below, the term "crude diisopropanolamine" is always understood to mean a mixture of the compounds represented by the formulas $HN(CH_2CH(OH)CH_3)_2$, $HN(CH(CH_3)CH_2OH)_2$, and $HN(CH(CH_3)CH_2OH)(CH_2CH(OH)CH_3)$ that is obtained in the reaction of propylene oxide and ammonia after removal of monoisopropanolamine and triisopropanolamine. It comprises about 89% by weight of $HN—(CH_2—CH(OH)CH_3)_2$ 8–10% by weight of $HN(CH(CH_3)—CH_2OH)(CH_2—CH(OH)CH_3)$ and 0.1–1% by weight of $HN—(CH(CH_3)—CH_2OH)_2$.

Example 1

At a hydrogen pressure of 3 MPa, 515 g of crude diisopropanolamine (3.87 mol) in 750 ml of liquid ammonia (30 mol) were stirred at 200° C. in the presence of 100 g of an Ni/Fe 85/15 catalyst (comprising 85% by weight of Ni and 15% by weight of Fe) for two hours. This resulted in a final pressure of 15.9 MPa. The apparatus was then vented, the crude dimethylpiperazine mixture was dissolved in 1.5 liter of methanol and freed from the catalyst by filtration, and the solution was evaporated at atmospheric pressure using a 20 cm packed column containing Raschig rings as glass packing.

The entire reaction mixture obtained was distilled at atmospheric pressure over a column. At a boiling point of 150–153° C., 344 g of distillate (76.6%, based on the crude diisopropanolamine employed) and 26 g of distillation residue were obtained.

For analysis of the composition, a 0.5 g sample of this distillate was mixed at room temperature with about 2 g of acetic anhydride and, with gentle heating, allowed to stand for one hour. This acetylated sample was then analyzed by gas chromatography using a 20 m SE 30 capillary column and found to comprise the following:

2.01% of cis-2,5-dimethylpiperazine
4.88% of trans-2,5-dimethylpiperazine
84.94% of cis-2,6-dimethylpiperazine
7.0% of trans-2,6-dimethylpiperazine The entire distillate was recrystallized in a mixture of 200 ml of isopropanol and 650 ml of light benzine, the mixture slowly being cooled first to room temperature and then to 0° C. The crystals were collected by filtration and dried under reduced pressure, giving 235.5 g of product (52.5%, based on the crude diisopropanolamine employed) having a melting point of 112.5–113° C. The product was analyzed by gas chromatography as described above and found to comprise the following:

0% of cis-2,5-dimethylpiperazine
0% of trans-2,5-dimethylpiperazine
99.6% of cis-2,6-dimethylpiperazine
0.33% of trans-2,6-dimethylpiperazine Recrystallization gave 178 g of cis-2,6-dimethylpiperazine having a purity of 100% (1.78 mol) and a melting point of 113–114° C.

Thus, the overall yield was 46%, based on the crude diisopropanolamine employed (1.78 mol of cis-2,6-dimethylpiperazine, based on 3.87 mol of crude diisopropanolamine employed).

Example 2

At a hydrogen pressure of 3 MPa, 980 g of crude diisopropanolamine were stirred in 1.2 liter of liquid ammonia in the presence of 250 g of Raney cobalt at 200° C. for three hours. The apparatus was then vented, the crude dimethylpiperazine mixture was dissolved in 1.5 l of methanol and freed from the catalyst by filtration, and the solution was evaporated at atmospheric pressure using a 20 cm packed column containing Raschig rings as glass packing. After acetylation with acetic anhydride (as described in Example 1), the gas chromatogram gave the following values:

2.96% of cis-2,5-dimethylpiperazine
3.22% of trans-2,5-dimethylpiperazine
81.79% of cis-2,6-dimethylpiperazine
6.31% trans-2,6-dimethylpiperazine At 145–163° C. and under atmospheric pressure, the resulting residue was distilled over the column mentioned above to give 719 g of distillate having a melting point of 102° C. After acetylation with acetic anhydride (as described in Example 1), a sample of the distillate was analyzed by gas chromatography and found to comprise the following:

3.01% of cis-2,5-dimethylpiperazine
3.25% of trans-2,5-dimethylpiperazine
84.38% of cis-2,6-dimethylpiperazine
4.78% of trans-2,6-dimethylpiperazine The entire distillate was recrystallized in a mixture of 150 ml of isopropanol and 1500 ml of light benzine, the mixture being slowly cooled first to room temperature and then to 0° C. Filtration and drying of the crystals under reduced pressure gave 569 g of product having a melting point of 110° C. After acetylation, a sample of the crystals is analyzed by gas chromatography and found to comprise the following:

0.91% of cis-2,5-dimethylpiperazine
1.1% of trans-2,5-dimethylpiperazine
95.08% of cis-2,6-dimethylpiperazine
2.0% of trans-2,6-dimethylpiperazine Recrystallization gave 502 g of 100% pure cis-2,6-dimethyl-piperazine having a melting point of 113–114° C.

Additional cis-2,6-dimethylpiperazine could be isolated from the mother liquor, so that an overall yield of 63% of theory was achieved.

Example 3

Under an initial pressure of 3 MPa of hydrogen, 500 g of crude diisopropanolamine were stirred with 100 g of Raney nickel and 750 ml of liquid ammonia at 200° C. The final pressure was 154 bar. The apparatus was vented, the crude product mixture was dissolved in methanol and freed from the catalyst by filtration, and the filtrate was evaporated at atmospheric pressure using a 20 cm packed column containing Raschig rings as glass packing. After separation according to Example 1, a sample of the distillation residue was analyzed by gas chromatography and found to comprise the following:

| |
|---|
| 2.55% of cis-2,5-dimethylpiperazine |
| 3.73% of trans-2,5-dimethylpiperazine |
| 83.81% of cis-2,6-dimethylpiperazine |
| 5.65% of trans-2,6-dimethylpiperazine |

At atmospheric pressure, the entire residue was distilled over the above-mentioned column at 150–166° C. to give 367 g of dimethyl-piperazine distillate (85.6%, based on the crude diisopropanolamine employed) and 26 g of distillation residue. Acetylation and analysis by gas chromatography showed that the distillate comprised:

| |
|---|
| 2.61% of cis-2,5-dimethylpiperazine |
| 4.11% of trans-2,5-dimethylpiperazine |
| 84.49% of cis-2,6-dimethylpiperazine |
| 5.7% of trans-2,6-dimethylpiperazine |

One recrystallization of the distillate from a mixture of 260 ml of isopropanol and 1000 ml of light benzine afforded 246 g of dimethyl-piperazines which, according to analysis by gas chromatography, comprised 99.29% of cis-2,6- and 0.7% of trans-2,6-dimethylpiperazine. Recrystallization afforded 220 g of 100% pure cis-2,6-dimethylpiperazine (corresponding to 51.3% of theory, based on the crude diisopropanolamine employed). After workup of the mother liquor, a total of 253.5 g of cis-2,6-dimethylpiperazine were obtained (59% of theory, based on the crude dimethylpiperazine).

What is claimed is:

1. A process for preparing cis-2,6-dimethylpiperazine comprising reacting a diisopropanolamine mixture comprising at least 85% by weight $HN(CH_2CH(OH)CH_3)_2$, 5 to 10% by weight $HN(CH(CH_3)CH_2OH)(CH_2CH(OH)CH_3)$, and 0.1 to 2% by weight $HN(CH(CH_3)CH_2OH)_2$ with ammonia and hydrogen in the presence of a hydrogenation catalyst.

2. A process according to claim 1 wherein the diisopropanolamine mixture is obtained by reaction of propylene oxide with ammonia.

3. A process according to claim 1 wherein the hydrogenation catalyst is Raney nickel or Raney cobalt.

4. A process according to claim 1 wherein the hydrogenation catalyst is at least one metal or metal oxide selected from the group consisting of nickel, copper, cobalt, and iron.

5. A process according to claim 1 wherein the hydrogenation catalyst is a nickel- and iron-containing catalyst having a nickel content of at least 60% by weight and an iron content of at most 40% by weight.

6. A process according to claim 1 wherein 5 to 150 g of catalyst is used per mole of diisopropanolamine mixture.

7. A process according to claim 1 wherein 100 to 200 ml of ammonia in pure liquid form is used per mole of diisopropanolamine mixture.

8. A process according to claim 1 wherein hydrogen is used at a pressure of 1 to 12 MPa at a temperature of 100 to 250° C. over a period of 2 to 10 hours.

9. A process according to claim 1 wherein, after reacting the diisopropanolamine mixture with ammonia and hydrogen in the presence of the hydrogenation catalyst, the resulting reaction product is distilled and recrystallized to increase the selectivity for cis-2,6-dimethylpiperazine.

10. A process according to claim 9 wherein recrystallization is carried out using as solvent a mixture of one or more aliphatic alcohols and one or more hydrocarbons.

11. A process according to claim 1 wherein the sum of the % by weight for $HN—(CH_2—CH(OH)CH_3)_2$, $HN(CH(CH_3)—CH_2OH)_2$ and $HN(CH(CH_3)—CH_2OH)(CH_2—CH(OH)CH_3)$ is at least 97% by weight.

12. A process according to claim 1 wherein the diisopropanolamine mixture used does not contain any monoisopropanolamine or triisopropanolamine.

* * * * *